United States Patent
Nickisch et al.

(10) Patent No.: US 8,673,968 B2
(45) Date of Patent: Mar. 18, 2014

(54) PROGESTERONE ANTAGONISTS

(75) Inventors: Klaus Nickisch, Berlin (DE); James Cessac, Floresville, TX (US); Kesavaram Narkunan, San Antonio, TX (US); Baishakhi Das, San Antonio, TX (US)

(73) Assignee: Evestra, Inc., San Antonio, TX (US)

( * ) Notice: Subject to any disclaimer, the term of this patent is extended or adjusted under 35 U.S.C. 154(b) by 359 days.

(21) Appl. No.: 12/749,246

(22) Filed: Mar. 29, 2010

(65) Prior Publication Data

US 2010/0273759 A1 Oct. 28, 2010

Related U.S. Application Data

(60) Provisional application No. 61/166,921, filed on Apr. 6, 2009.

(51) Int. Cl.
*A61K 31/341* (2006.01)
*C07J 21/00* (2006.01)

(52) U.S. Cl.
USPC ............................................ 514/462; 540/28

(58) Field of Classification Search
USPC .......................................... 540/28; 514/462
See application file for complete search history.

(56) References Cited

U.S. PATENT DOCUMENTS

| 6,005,124 A | 12/1999 | Brands et al. |
| 6,768,014 B2 | 7/2004 | Kim et al. |
| 6,900,193 B1 | 5/2005 | Kim et al. |

FOREIGN PATENT DOCUMENTS

| EP | 0582338 | * 2/1994 |

OTHER PUBLICATIONS

Morphy et al., "Designed Multiple Ligands. An Emerging Drug Discovery Paradigm." J. Med. Chem. (2005), 48, 6523-6543.
Morphy et al., "The Physicochemical Challenges of Designing Multiple Ligands." J. Med. Chem. (2006), 49, 4961-4970.
Woo et al. "First Dual Aromatase-Sulfatase Inhibitors." J. Med. Chem. (2003), 46, 3193-3196.
Wood et al. "A letrazole-based dual aromatase-sulphatase inhibitor with in vivo activity." J. Steroid Biochem Mol Biol. (2005), 94, 123-130.
Numazawa et al. "Inhibition of Estrone sulfatase by aromatic inhibitor-based estrogen 3-sulfamates." Steroids (2006), 71, 371-379.
Jackson et al. "Dual aromatic-sulfatase inhibitors based on the anastrozole template: synthesis, in vitro SAR, molecular modeling and in vivo activity." Org. Biomol. Chem. (2007), 5, 2940-2952.
Woo et al. "Dual Aromatase-Sulfatase Inhibitors." J. Med. Chem. (2007), 50, 3540-3560.
Klijn et al. "Progesterone antagonists and progesterone receptor modulators in the treatment of breast cancer." Steroids (2000), 65, 825-830.
Wiehle et al. Anti-progestins suppress the growth of established tumors induced by 7,12-dimethylbenz(a) anthracene: Comparison between RU486 and a new 21-substituted-19-norprogestin. Oncology Reports, (2007), 18, 167-174.
Brodie et al. "Aromatase Inhibitors in advanced breast cancer: Mechanism of action and clinical implications." J. Steroid Biochem. Molec. Biol. (1998), 66, 1-10.
Furet et al. "Aromatase Inhibitors: Synthesis, biological activity, and binding mode of azole-type compounds." J. Med. Chem. (1993), 36, 1393-1400.
Teutsch et al. "Synthesis of a fluorescent steroid derivative with high affinities for the glucocorticoid and progesterone receptors." Steroids (1994), 59, 22-26.
Rao et al. A practical large-scale synthesis of 17-acetoxy-11-(4-N,N-dimethylaminophenyl)-19-norpregna-4,9-diene-3,20-dione (CDB-2914). Steroids (2000), 65, 395-400.
Giangrande et al. "The Opposing Transcriptional Activities of the Two Isoforms of the Human Progesterone Receptor Are Due to Differential Cofactor Binding." Mol Cell Biol (2000) 20:3102-3115.
Jiang et al. "New progesterone receptor antagonists: Phosphorus-containing 11β-aryl-substituted steroids." Bioorg Med Chem (2006) 14:6726-6732.
Intent to Grant for EP counterpart application No. EP 2417148 issued Dec. 5, 2012.
Teutsch et al. entitled "History and Persprectives of Antiprogetins from the Chemist's Point of View" Human Reporduction, vol. 9, Supplement 1, 1994, p. 12-31.
Selective progesterone receptor modulators, Wikipedia, Jan. 16, 2013.

* cited by examiner

*Primary Examiner* — Barbara P Badio
(74) *Attorney, Agent, or Firm* — Meyertons, Hood, Kivlin, Kowert & Goetzel, P.C.; Eric B. Meyertons

(57) ABSTRACT

Described herein are compounds which exhibit progesterone antagonistic effects and methods of treating cancer using such compounds.

2 Claims, 1 Drawing Sheet

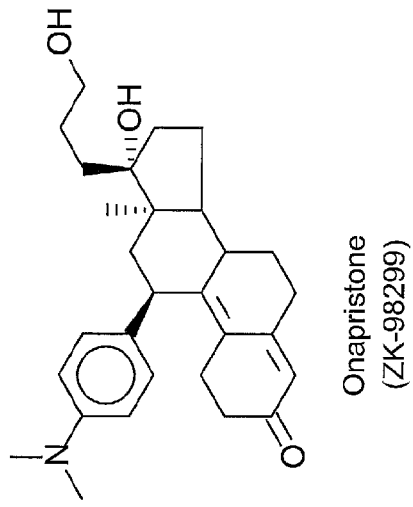
Onapristone
(ZK-98299)
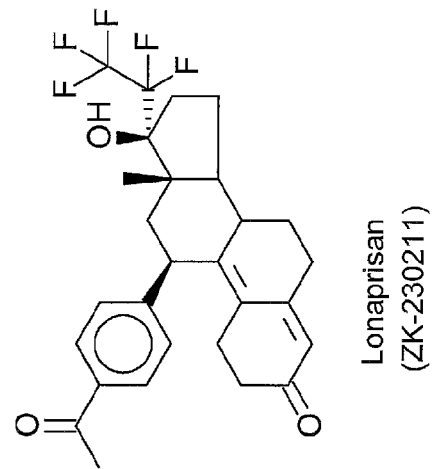
Lonaprisan
(ZK-230211)
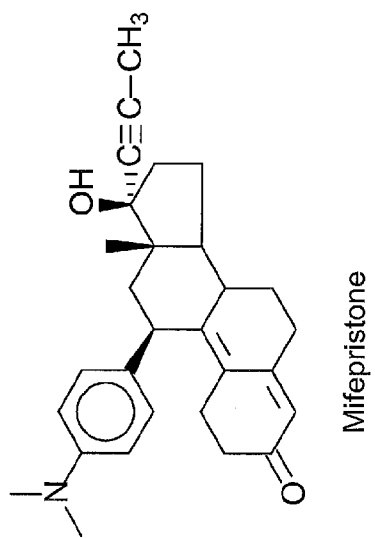
Mifepristone
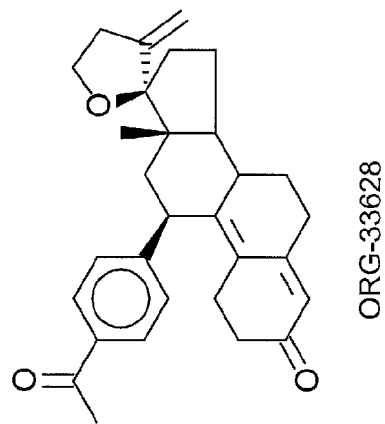
ORG-33628
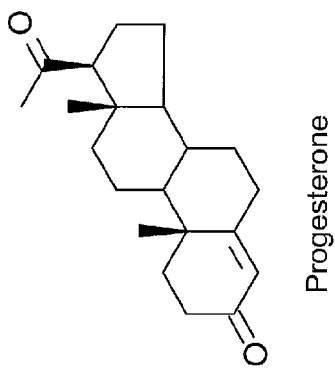
Progesterone
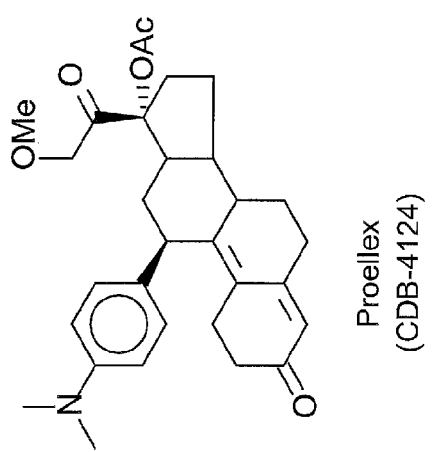
Proellex
(CDB-4124)

PROGESTERONE ANTAGONISTS

PRIORITY CLAIM

This application claims the benefit of U.S. Provisional Application No. 61/166,921 filed on Apr. 6, 2009.

BACKGROUND OF THE INVENTION

1. Field of the Invention

The present invention relates to suppressing the growth of cancer and other proliferative diseases by the administering of novel compounds that exhibit progesterone antagonism. The present invention also relates to processes of preparation and the use in therapy of such novel compounds.

2. Description of the Relevant Art

In the past, progesterone antagonists have been postulated to be of potential benefit in the treatment of breast cancer where the primary lesion contains both estrogen and progesterone receptors. In a recent study of an in vivo rat model of progesterone receptor positive breast cancer, it was shown that the administration of a new antiprogestin (PROELLEX, CDB-4124) resulted in a regression of tumor size as well as a decrease in the development of new tumors. FIG. 1 shows a series of selected progesterone antagonists that have been shown to be effective in vitro and in vivo. The prototype antagonist, Mifepristone (see FIG. 1), is characterized by the 19-nor-4,9-diene steroid nucleus, the 17α-propynyl-17β-hydroxy functionality, and the 11β-(4-dimethylamino)phenyl functional group which is believed to be responsible for its antagonistic activity. While Mifepristone is a potent progesterone antagonist, its long-term clinical use is limited due to its overt glucocorticoid receptor antagonism. Subsequent development undertaken by several groups has led to the discovery of several novel progesterone antagonists that are both more active than Mifepristone and more dissociated in relation to glucocorticoid antagonism. Some notable examples as outlined above in FIG. 1 and include Onapristone, ORG-33628, PROELLEX, and Lonaprisan (ZK-230211).

Of these examples, Lonaprisan is most notable in that it exhibits the highest antiprogestagenic activity and displays only marginal antiglucocorticoid effects. The high activity of Lonaprisan in comparison with the other analogs is somewhat surprising in that the normal effect on the introduction of a 17α-alkyl group in steroids is to increase its interaction with the androgen receptor, an effect not seen with this compound. However, the substitution of fluorine for hydrogen can often induce significant biochemical changes in a pharmaceutical molecule while causing only a slight change in its shape.

While antiprogestin therapies have been effective in the treatment of some forms of cancer (including breast cancers), there is still a need to develop more effective therapies.

SUMMARY OF THE INVENTION

In one embodiment, a progesterone antagonist has the structure of formula (I):

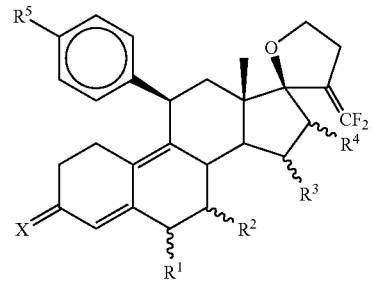

In which
$R^1$ is a hydrogen atom, a straight-chain $C_1$-$C_5$ alkyl group, a branched $C_1$-$C_5$ alkyl group, a $C_3$-$C_5$ cycloalkyl group, or a halogen atom;
$R^2$ is a hydrogen atom, a straight-chain $C_1$-$C_5$ alkyl group a branched $C_1$-$C_5$ alkyl group, a $C_3$-$C_5$ cycloalkyl group, or a halogen atom; or
$R^1$ and $R^2$ together are a methylene group;
$R^3$ is a hydrogen atom, a straight-chain $C_1$-$C_5$ alkyl group a branched $C_1$-$C_5$ alkyl group, a $C_3$-$C_5$ cycloalkyl group, or a halogen atom;
$R^4$ is a hydrogen atom, a straight-chain $C_1$-$C_5$ alkyl group a branched $C_1$-$C_5$ alkyl group, a $C_3$-$C_5$ cycloalkyl group, or a halogen atom; or
$R^3$ and $R^4$ together are an additional bond or a methylene group;
$R^5$ is a radical Y or an aryl radical that is optionally substituted with Y, wherein Y is a hydrogen atom, a halogen atom, —$OR^6$, —$NO_2$, —$N_3$, —CN, —$NR^{6a}R^{6b}$, —$NHSO_2R^6$, —$CO_2R^6$, $C_1$-$C_{10}$ alkyl, $C_1$-$C_{10}$ substituted alkyl, $C_1$-$C_{10}$ cycloalkyl, $C_1$-$C_{10}$ alkenyl, $C_1$-$C_{10}$ alkynyl, $C_1$-$C_{10}$ alkoxy, $C_1$-$C_{10}$ alkanoyloxy, benzoyloxy, arylacyl, $C_1$-$C_{10}$-alkylacyl, $C_1$-$C_{10}$-cycloalkylacyl, $C_1$-$C_{10}$ hydroxyalkyl, aryl or arylalkyl, a five or six membered heterocyclic radical containing up to three heteroatoms;
$R^{6a}$ and $R^{6b}$ are the same or different and represent a hydrogen atom or a $C_1$-$C_{10}$ alkyl group, $R^6$ is a hydrogen atom or $C_1$-$C_{10}$ alkyl,
when Y is a —$NR^{6a}R^{6b}$ radical, Y may be in the form of a physiologically compatible salt formed by reaction of an acid;
when Y is —$CO_2R^6$, $R^6$ may represent a cation of a physiologically compatible salts formed by reaction with a base; and
the wavy lines represent that the substituent can be in an α- or β-orientation.

BRIEF DESCRIPTION OF THE DRAWINGS

Advantages of the present invention will become apparent to those skilled in the art with the benefit of the following detailed description of embodiments and upon reference to the accompanying drawings in which:

FIG. 1 depicts several known progesterone antagonists.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular compounds, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

Unless defined otherwise, all technical and scientific terms used herein have the same meaning as commonly understood by one of ordinary skill in the art.

Chemical structures depicted herein that do not designate specific stereochemistry are intended to embrace all possible stereochemistries. For example, wavy lines represent that the substituent in question can be in α- or β-position.

It will be appreciated by those skilled in the art that some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral center that, while it can exist as two or more stereoisomers, is isolated in greater than about 95% excess of one of the possible stereoisomers. As used herein a compound that has one or more chiral centers is considered to be "optically active" when isolated or used as a single stereoisomer.

The term "alkyl" as used herein generally refers to a chemical substituent containing the monovalent group $C_nH_{2n}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "substituted alkyls" as used herein generally refers to alkyl radicals that include one or more functional groups attached to any carbon of the alkyl radical. Functional groups include, but are not limited to, aryl, aralkyl, acyl, halogens, hydroxyl, amino, alkylamino, acylamino, acyloxy, alkoxy, and mercapto. As used herein the term "substituted lower alky" refers to an alkyl residue having from 1-6 carbon atoms and one or more functional groups attached to any carbon of the alkyl radical.

The term "cycloalkyl" denotes a ring composed of carbon atoms. Examples of cycloalkyl groups include, but are not limited to, cyclopropyl-, cyclobutyl, cyclopentyl and cyclohexyl.

As used herein the terms "alkenyl" and "olefin" generally refer to any structure or moiety having the unsaturation C=C. Examples of alkenyl radicals include, but are not limited to vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl.

As used herein, the term "alkynyl" generally refers to any structure or moiety having the unsaturation C≡C. Examples of alkynyl radicals include, but are not limited to: ethynyl, 1-propynyl, 2-propynyl, 1-butynyl, 2-butynyl, and 3-butynyl.

The term "aryl" is used to refer to an aromatic substituent which may be a single ring or multiple rings which are fused together, linked covalently, or linked to a common group such as an ethylene moiety. Aromatic ring(s) include but are not limited to phenyl, naphthyl, biphenyl, diphenylmethyl, and 2,2-diphenyl-1-ethyl. The aryl group may also be substituted with substituents including, but not limited to, alkyl groups, halogen atoms, nitro groups, carboxyl groups, alkoxy, and phenoxy to give a "substituted aryl group." Substituents may be attached at any position on the aryl radical which would otherwise be occupied by a hydrogen atom.

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term "acyloxy" is used herein to refer to an organic radical derived from an organic acid by the removal of a hydrogen. The organic radical can be further substituted with one or more functional groups including, but not limited to, alkyl, aryl, aralkyl, acyl, halogen, amino, thiol, hydroxyl, alkoxy. etc. Suitable acyloxy groups include, for example, acetoxy, i.e., $CH_3COO-$, which is derived from acetic acid.

The term "halogen" is used herein to refer to fluorine, bromine, chlorine and iodine atoms.

The term "hydroxyl" is used herein to refer to the group —OH.

The term "alkylacyl" denotes groups —C(O)R where R is alkyl or substituted alkyl.

The term "arylacyl" denotes groups —C(O)R where R is aryl or substituted aryl.

The term "cycloalkylacyl" denotes groups —C(O)R where R is a cycloalkyl or substituted cycloalkyl such as, for example, cyclopropylacyl-, cyclopentylacyl and cyclohexylacyl.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogs of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromenyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "alkyl carbonate" is used herein to refer to the group —OC(O)OR, where R is alkyl, substituted alkyl, aryl, or substituted aryl as defined herein.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

Progesterone Antagonists

In one embodiment, a progesterone antagonist has the structure of formula (I):

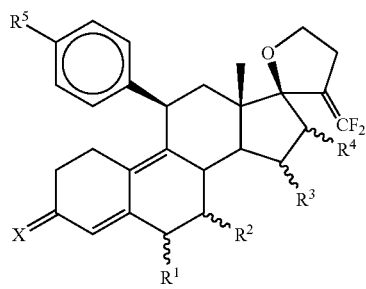

In which
$R^1$ is a hydrogen atom, a straight-chain $C_1$-$C_5$ alkyl group, a branched $C_1$-$C_5$ alkyl group, a $C_3$-$C_5$ cycloalkyl group, or a halogen atom;
$R^2$ is a hydrogen atom, a straight-chain $C_1$-$C_5$ alkyl group a branched $C_1$-$C_5$ alkyl group, a $C_3$-$C_5$ cycloalkyl group, or a halogen atom; or
$R^1$ and $R^2$ together are a methylene group;
$R^3$ is a hydrogen atom, a straight-chain $C_1$-$C_5$ alkyl group a branched $C_1$-$C_5$ alkyl group, a $C_3$-$C_5$ cycloalkyl group, or a halogen atom;
$R^4$ is a hydrogen atom, a straight-chain $C_1$-$C_5$ alkyl group a branched $C_1$-$C_5$ alkyl group, a $C_3$-$C_5$ cycloalkyl group, or a halogen atom; or
$R^3$ and $R^4$ together are an additional bond or a methylene group;
$R^5$ is a radical Y or an aryl radical that is optionally substituted with Y, wherein Y is a hydrogen atom, a halogen atom, —$OR^6$, —$NO_2$, —$N_3$, —CN, —$NR^{6a}R^{6b}$, —$NHSO_2R^6$, —$CO_2R^6$, $C_1$-$C_{10}$ alkyl, $C_1$-$C_{10}$ substituted alkyl, $C_1$-$C_{10}$ cycloalkyl, $C_1$-$C_{10}$ alkenyl, $C_1$-$C_{10}$ alkynyl, $C_1$-$C_{10}$ alkoxy, $C_1$-$C_{10}$ alkanoyloxy, benzoyloxy, arylacyl, $C_1$-$C_{10}$-alkylacyl, $C_1$-$C_{10}$-cycloalkylacyl, $C_1$-$C_{10}$ hydroxyalkyl, aryl or arylalkyl, a five or six membered heterocyclic radical containing up to three heteroatoms;
$R^{6a}$ and $R^{6b}$ are the same or different and represent a hydrogen atom or a $C_1$-$C_{10}$ alkyl group, $R^6$ is a hydrogen atom or $C_1$-$C_{10}$ alkyl,
when Y is —$NR^{6a}R^{6b}$ radicals, Y may be in the form of a physiologically compatible salt formed by reaction of an acid;
when Y is —$CO_2R^6$, $R^6$ may represent a cation of a physiologically compatible salts formed by reaction with a base; and
the wavy lines represent that the substituent can be in an α- or β-orientation.

In an embodiment, a progesterone antagonist has the structure of formula (II):

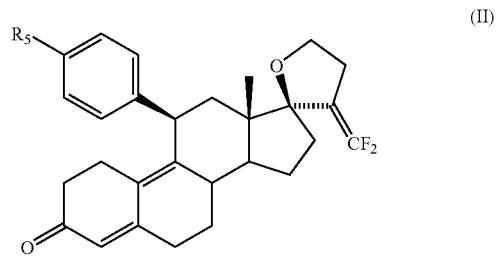

Where $R^5$ is a radical Y or an aryl radical that is optionally substituted with Y, wherein Y is a hydrogen atom, a halogen atom, —$OR^6$, —$NO_2$, —$N_3$, —CN, —$NR^{6a}R^{6b}$, —$NHSO_2R^6$, —$CO_2R^6$, $C_1$-$C_{10}$ alkyl, $C_1$-$C_{10}$ substituted alkyl, $C_1$-$C_{10}$ cycloalkyl, $C_1$-$C_{10}$ alkenyl, $C_1$-$C_{10}$ alkynyl, $C_1$-$C_{10}$ alkoxy, alkanoyloxy, benzoyloxy, arylacyl, $C_1$-$C_{10}$-alkylacyl, $C_1$-$C_{10}$-cycloalkylacyl, $C_1$-$C_{10}$ hydroxyalkyl, aryl or arylalkyl, a five or six membered heterocyclic radical containing up to three heteroatoms;
$R^{6a}$ and $R^{6b}$ are the same or different and represent a hydrogen atom or a $C_1$-$C_{10}$ alkyl group, $R^6$ is a hydrogen atom or $C_1$-$C_{10}$ alkyl, when Y is —NR$^{6a}$R$^{6b}$ radicals, Y may be in the form of a physiologically compatible salt formed by reaction of an acid;

when Y is —CO$_2$R$^6$, R$^6$ may represent a cation of a physiologically compatible salts formed by reaction with a base.

In an embodiment, a progesterone antagonist has the structure of formula (II):

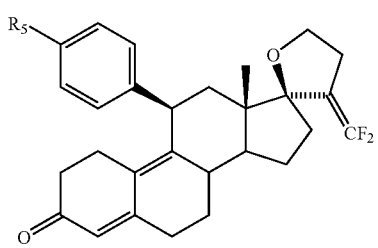

(II)

Where R$^5$ is —OR$^6$, —NR$^{6a}$R$^{6b}$, C$_1$-C$_{10}$ alkylacyl, C$_1$-C$_{10}$ alkenyl, or a five or six membered heterocyclic radical containing up to three heteroatoms; and Where R$^{6a}$ and R$^{6b}$ are the same or different and represent a hydrogen atom or a C$_1$-C$_{10}$ alkyl group, R$^6$ is a hydrogen atom or C$_1$-C$_{10}$ alkyl;

when Y is a —NR$^{6a}$R$^{6b}$ radical, Y may be in the form of a physiologically compatible salt formed by reaction of an acid.

In an embodiment, a progesterone antagonist has the structure of formula (II) where R$^5$ is —OR$^6$, and where R$^6$ is a hydrogen atom or C$_1$-C$_{10}$ alkyl.

In an embodiment, a progesterone antagonist has the structure of formula (II) where R$^5$ is —NR$^{6a}$R$^{6b}$ and where R$^{6a}$ and R$^{6b}$ are the same or different and represent a hydrogen atom or a C$_1$-C$_{10}$ alkyl group, or —NR$^{6a}$R$^{6b}$ is in the form of a physiologically compatible salt formed by reaction of an acid.

In an embodiment, a progesterone antagonist has the structure of formula (II) where R$^5$ is C$_1$-C$_{10}$ alkylacyl.

In an embodiment, a progesterone antagonist has the structure of formula (II) where R$^5$ is C$_1$-C$_{10}$ alkenyl.

In an embodiment, a progesterone antagonist has the structure of formula (II) where R$^5$ is a five or six membered heterocyclic radical containing up to three heteroatoms.

Specific examples of compounds having the formula (I) include the following compounds:

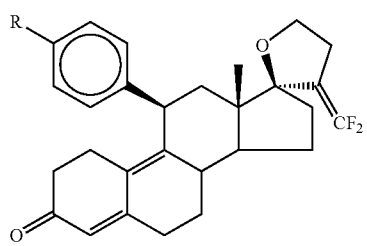

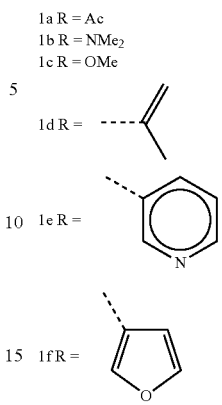

1a R = Ac
1b R = NMe$_2$
1c R = OMe

1d R =

1e R =

1f R =

Synthesis of compounds 1a, 1b, 1c, 1d, 1e and 1f may be prepared according to the general Scheme 1.

Scheme 1

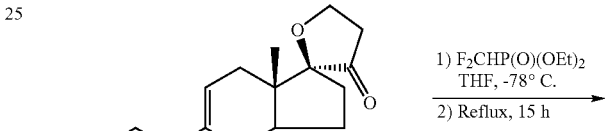
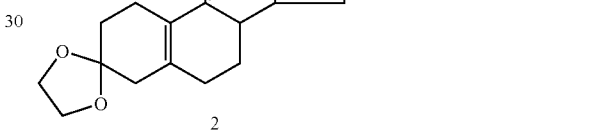

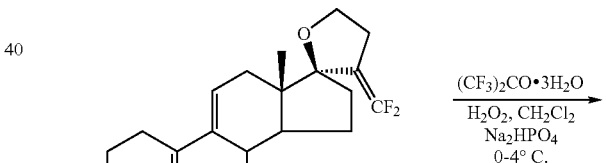

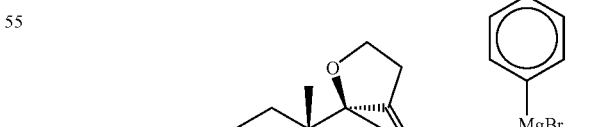
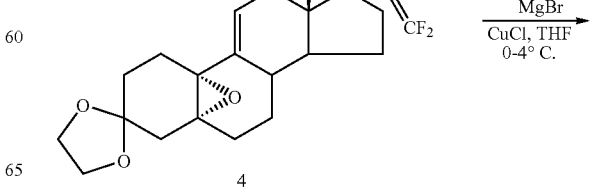

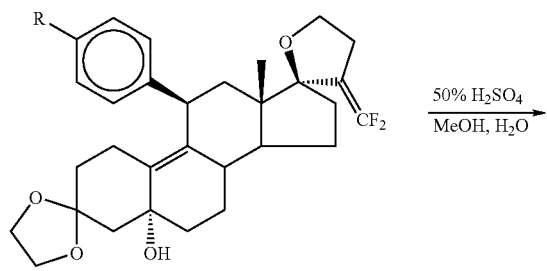

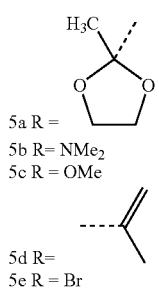

5a R = 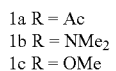
5b R = NMe₂
5c R = OMe

5d R = 
5e R = Br

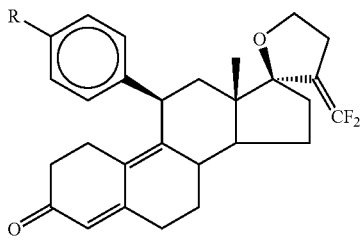

1a R = Ac
1b R = NMe₂
1c R = OMe

1d R = 
1g R = Br

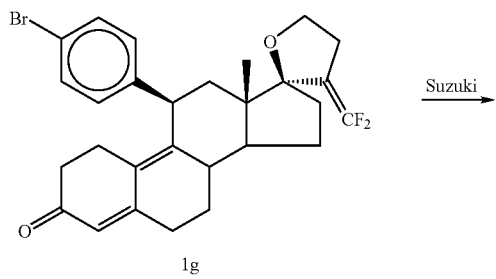

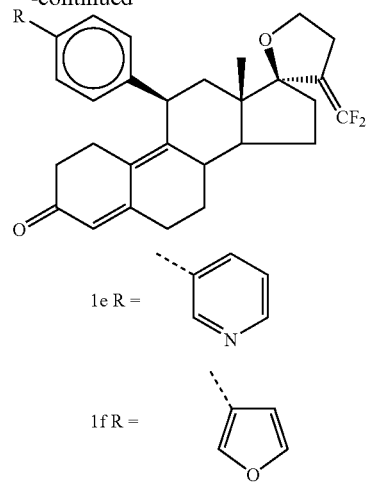

1e R = [pyridin-3-yl]

1f R = [furan-3-yl]

The intermediate 17-spirodihydrofuran-3'(2'H)-one (2) may be synthesized following the procedure of Jiang et al. "New progesterone receptor antagonists: Phosphorus-containing 11β-aryl-substituted steroids." Bioorg Med Chem (2006) 14:6726-6732. Subsequent Wittig-Horner reaction with the reagent prepared from difluoromethyldiphenylphosphine oxide gives the exocyclic-difluoromethylene intermediate (3). Subsequent epoxidation, conjugate Grignard addition and hydrolysis will give the targeted compounds 1a-1f.

Any suitable route of administration may be employed for providing a patient with an effective dosage of the progesterone antagonist compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally. The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

The agonist and antagonist actions of the described progesterone antagonists may be tested using breast cancer cells. Established human breast cancer cell lines, such as MCF-7, T47D, MDMB231 and SKBR-3 and derivatives of these cell lines with/without PR expression, may be used to test the effect of the novel progesterone antagonists.

In one embodiment, a progesterone receptor reporter gene system may be used to evaluate the agonist and antagonist activities of the subject progesterone antagonists. Agonist and antagonist activities may further verified using a progesterone transactivation assay along with a proliferative effect assay of progesterone antagonists on these cells.

The in vitro biological activity of the progesterone antagonists may be compared to the activity of controls P4 (agonist) and RU486 (antagonist) using a cell based progesterone receptor element (PRE)-luciferase assay, as described in Giangrande et al. "The Opposing Transcriptional Activities of the Two Isoforms of the Human Progesterone Receptor Are Due to Differential Cofactor Binding." Mol Cell Biol (2000) 20:3102-3115, which is incorporated herein by reference. The luciferase (luc) reporters 2×PRE-tk-luc contain two copies of the progesterone response element (PRE) upstream of a thymidine kinase (tk) promoter. This vector has been used in numerous studies to test the effect of various progesterone antagonists. Test progesterone antagonists may be evaluated for PR agonism and antagonism in this assay. Testing the PR agonist and antagonist activities with different concentrations of the progesterone antagonists may be used to determine their ability to block or enhance the PRE-luciferase activity and as a measure of their ability to bind and influence PR regulation using the T47D breast cancer cell line. This cell line expresses both human PR-A and PR-B forms of PR and is widely used for testing P4/PR effects. After determining the optimum concentration, the progesterone antagonists may be tested in different cell lines at the optimum concentration. Also their agonism and antagonism may be tested in PR-dependent transactivation assay.

In the luciferase assay, the reporter vector is first transfected into cells. After a limited amount of time, the cells are lysed and the substrate of luciferase, luciferin, is introduced into the cellular extract along with Mg and excess ATP. Under these conditions, luciferase enzyme expressed by the reporter vector will catalyze the oxidative carboxylation of luciferin. The luminescence from this chemical reaction can be read and quantified by a luminometer. The amount of light detected from the cell lysate correlates directly with the binding activity of the transcription factor. The Empty Control Vector may be used as a negative control for subtracting any background. The Empty Control Vector does not contain the transcription factor response element insert; it only contains the minimal TATA promoter and does not respond to any specific transactivation compound.

Transfections may be performed in 80% confluent 24 h old cultures. For transient transfection, 200 mg/well of PRE-luciferase DNA may be used. Lipofectamine 2000 may be used for transfection following the manufacturer's instructions. Unless otherwise specified, 5 ng/well of other optical reporters may be used for transfection normalization in the transient transfection studies. The cells may be assayed after 24 h incubation at 37° C. at 5% $CO_2$ with a specific concentration for each progesterone antagonist. The transfected cells may be lysed in 200 ml of ice-cold 1× passive lysis buffer supplied by Promega and may then be shaken for 15 min on ice. The cell lysates may be centrifuged for 5 min at $1.3 \times 10^4$ g at 4° C. to remove cell debris. To determine *Renilla* luciferase activity, 20 ml of supernatant may be assayed by addition of 0.5 mg of coelenterazine in 100 ml of 0.5M sodium PBS at pH 7.0 (PBS), followed by photon counting in the luminometer (model T 20/20; Turner Designed, Sunnyvale, Calif.) for 10 sec. Firefly luciferase activity may be determined as described for *Renilla* luciferase activity, except 100 ml of LARII substrate from Promega will be used. Protein concentrations in cell lysates may be determined by Bradford Assay (Bio-Rad Laboratories, Hercules, Calif.). *Renilla* luciferase activities may be normalized for protein content and for transfection efficiency using firefly luciferase activity and will be expressed as relative light units (RLU) per microgram protein per minute of counting.

To measure activation of PR, an ELISA-based PR transactivation assay may be performed as per manufacturer's guidelines (Panomics). Briefly, the nuclear lysates of cells or tumors may be generated as described by the manufacturer. Binding of ligand (agonist or antagonist) such as P4 or RU486 induces a conformational change in the receptor, allowing the receptor to bind to specific DNA sites; progesterone response elements. Activated PR from nuclear extracts may be allowed to bind to the PR consensus binding site (PR probe) on a biotinylated oligonucleotide. These oligonucleotides may then be immobilized on a streptavidin-coated 96-well plate. The PR bound to the oligonucleotide may be detected by an antibody directed against PR. An additional horseradish peroxidase-conjugated secondary antibody may provide colorimetric readout quantified by reading absorbance at 450 nm.

Using PRE-Luciferase assay and further validated with ELISA-based PR transactivation, it is possible to determine the agonist and antagonist activities of the progesterone antagonists. If mixed activity is seen, pure antagonist compounds may be tested to determine their efficacy in in vivo animal models. Further testing may be performed to determine the agonist and antagonist's activity on other reproductive tissues, especially for use in breast cancer treatment and prevention.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

3,3-Ethylenedioxy-21,21-difluoro-17,23-epoxy-19, 24-dinor-17α-chola-5(10),9(11),20-triene (3)

To a solution of diisopropylamine (0.95 mL, 6.8 mmol) in THF (10 mL) at −78° C., n-BuLi (2.7 mL, 2.5 M, 6.8 mmol) was introduced and stirred for 30 minutes. A solution of diethyl difluoromethylphosphonate (1.1 mL, 6.8 mmol) in THF (10 mL) was added and stirred for 1 hr at −78° C. Finally, a solution of 3,3-Ethylenedioxy-4',5'-dihydrospiro[estra-5 (10),9(11)-diene-17β,2'(3'H)-furan]-3'-one (2) (Jiang et al., *Bioorganic and Medicinal Chemistry*, 2006, 14, 6726) (1.0 g, 2.7 mmol) in THF (10 mL) was added dropwise, stirred for 30 minutes at −78° C., slowly warmed to room temperature during 1 hr and heated to reflux for 15 hrs. The reaction mixture was quenched with water (30 mL) and extracted with ethyl acetate (3×25 mL). The combined organic layer was washed once with brine, dried over sodium sulfate and evaporated in vacuo to afford crude product. Purification was carried out on silica gel using 10% ethyl acetate in hexane to afford 400 mg (37%) of the required product (15).

$^1$H NMR (δ, 300 MHz) 0.83 (s, 3H), 1.1-2.9 (m, 20H), 3.60-3.95 (m, 2H), 3.96 (s, 4H), 5.49 (bs, 1H). $^{13}$C NMR (75 MHz) 13.8, 23.9, 24.6, 27.6, 28.4, 31.2, 31.4, 33.02, 36.9, 38.6, 41.3, 46.79, 46.82, 64.4, 64.5, 65.1, 93.6 (t, J=3.9 Hz), 95.1 (dd, J=17.9, 19.5 Hz), 108.1, 117.6, 126.1, 130.3, 136.5, 150.9 (dd, J=282, 280 Hz).

EXAMPLE 2

3,3-Ethylenedioxy-21,21-difluoro-5α,10α;17,23-bisepoxy-19,24-dinor-17α-chola-9(11),20-diene (4)

Hydrogen peroxide (0.18 mL, 30%, 1.6 mmol) was added to an ice-cold solution of hexafluoroacetone trihydrate (350 mg, 1.6 mmol) in dichloromethane (3 mL). Solid $Na_2HPO_4$ (180 mg, 1.3 mmol) was introduced, and the reaction mixture was stirred for 1 hr at 0° C. An ice-cold solution of (3) (400 mg, 1 mmol) in dichloromethane (3 mL) was added and the mixture was stirred at 0 C for 3 hrs then at 5 C for 15 hrs. The reaction mixture was diluted with dichloromethane (15 mL) and washed with 10% sodium sulfite solution (15 mL), water, dried over sodium sulfate and concentrated under vacuum to obtain a mixture of crude epoxides. Separation of isomeric epoxides was carried out on a silica gel column using 10% ethyl acetate in hexane to afford 230 mg (55%) of pure α-isomer (44).

$^1$H NMR (δ, 300 MHz) 0.85 (s, 3H), 1.1-2.9 (m, 20H), 3.6-4.0 (m, 6H), 5.8-6.0 (m, 1H).

EXAMPLE 3

3,3-Ethylenedioxy-21,21-difluoro-5α-hydroxy-11β-{4'-[1',1'-(ethylenedioxy)-ethyl]phenyl}17,23-epoxy-19,24-dinor-17α-chola-9(10),20-diene (5a)

A slurry of magnesium (85 mg, 3.5 mmol) in THF (5 mL) containing a crystal of iodine was taken and heated to reflux for 10 minutes to become colorless. A solution of 2-(4-bromophenyl)-2-methyl-1,3-dioxolane (835 mg, 3.5 mmol) in THF (5 mL) was introduced during 5 minutes and allowed to reflux for 1 hr. The reaction mixture was cooled under ice and solid CuCl (100 mg, 1.0 mmol) was added to the mixture. The mixture was stirred at 0 C for 30 minutes. Finally a solution of (4) (480 mg, 1.15 mmol) in THF (5 mL) was added into the cuprate solution and allowed to stir for 2 hrs at 0 C. After this time the reaction mixture was quenched with aqueous ammonium chloride solution (30 mL) and extracted with ethyl acetate (3×25 mL). The combined organic layer was washed further with water and brine, dried over sodium sulfate and evaporated in vacuo to afford crude product. Purification was carried out on silica gel using 25% ethyl acetate in hexane to afford 350 mg (52%) of the required product (5a).

$^1$H NMR (δ, 300 MHz) 0.45 (s, 3H), 1.0-2.9 (m, 24H), 3.6-4.1 (m, 10H), 4.20 (d, J=7.4 Hz, 1H), 4.39 (s, 1H), 6.75 (d, J=8.5 Hz, 1H), 7.12 (d, J=8.2 Hz, 2H), 7.26-7.32 (m, 2H). $^{13}$C NMR (75 MHz) 14.3, 23.2, 23.9, 24.1, 27.4, 28.2, 32.57, 32.60, 35.0, 38.2, 39.0, 39.4, 40.8, 47.3, 48.0 (t, J=1.9 Hz), 49.48, 49.52, 64.04, 64.3, 64.4, 64.5, 64.6, 65.2, 70.2, 93.8 (t, J=3.9 Hz), 94.4 (dd, J=17.1, 19.8 Hz), 108.7, 108.8, 114.9, 125.1, 126.6, 126.9, 133.9, 134.3, 140.3, 146.5, 150.8 (t, J=282 Hz), 156.1

EXAMPLE 4

21,21-difluoro-11β-(4'-acetyl)phenyl-17,23-epoxy-19,24-dinor-17α-chola-4,9,20-triene (1a)

To a solution of 5a (350 mg, 0.6 mmol) in methanol (5 mL) at 0 C, 50% sulfuric acid (0.35 mL) was introduced and the mixture was allowed to stir at room temperature for 2 hrs. The reaction mixture was quenched with sodium bicarbonate solution (5 mL) and extracted with dichloromethane (3×15 mL). The combined organic layer was washed further with water and brine, dried over sodium sulfate and evaporated in vacuo to afford crude product. Purification was carried out on a silica gel column using 25% ethyl acetate in hexane to afford 250 mg (88%) of the desired product (1a).

$^1$H NMR (δ, 300 MHz) 0.52 (s, 3H), 1.1-2.9 (m, 19H), 2.57 (s, 3H), 3.70-4.0 (m, 2H), 4.37 (d, J=7.2 Hz), 5.77 (m, 1H), 7.25 (d, J=8.1 Hz, 2H), 7.87 (d, J=8.1 Hz, 2H). $^{13}$C NMR (75 MHz) 14.6, 23.6, 25.9, 26.6, 27.5, 28.4, 31.05, 32.7, 32.8, 36.8, 39.1, 40.79, 40.84, 48.4, 49.67, 49.72, 65.4, 93.6 (t, J=3.9 Hz), 94.7 (dd, J=17, 20 Hz), 123.4, 127.3, 128.8, 130.0, 135.1, 144.4, 150.6, 151.0 (t, J=282 Hz), 156.2, 197.6, 199.2.

EXAMPLE 5

3,3-Ethylenedioxy-21,21-difluoro-5α-hydroxy-11β-[4'-(dimethylamino)-phenyl]-17,23-epoxy-19,24-dinor-17α-chola-9(10),20-diene (5b)

Following the procedure outlined for the synthesis of compound (5a), the Grignard reagent prepared from 4-bromo-dimethylaniline was reacted with compound (4) and CuCl in THF to give after workup the required product (5b)

$^1$H NMR (δ, 300 MHz) 0.54 (s, 3H), 1.10-2.85 (m, 21H), 2.91 (s, 6H), 3.7-4.2 (m, 7H), 4.33 (s, 1H), 6.64 (d, J=8.7 Hz, 2H), 7.02 (d, J=8.6 Hz, 2H).

EXAMPLE 6

21,21-difluoro-11β-[4'-(dimethylamino)phenyl]-17,23-epoxy-19,24-dinor-17α-chola-4,9,20-triene (1b)

Following the procedure outlined for the synthesis of compound (1a), the Grignard adduct (5b) was hydrolyzed in 50% sulfuric acid to give after workup the required product (1b)

$^1$H NMR (δ, 300 MHz) 0.62 (s, 3H), 1.0-2.9 (m, 19H), 2.93 (s, 6H), 3.7-4.0 (m, 2H), 4.27 (d, J=6.9 Hz, 1H), 5.76 (s, 1H), 6.66 (d, J=8.8 Hz, 2H), 6.99 (d, J=8.7 Hz, 2H).

EXAMPLE 7

3,3-Ethlenedioxy-21,21-difluoro-5α-hydroxy-11β-(4'-methoxyphenyl]-17,23-epoxy-19,24-dinor-17α-chola-9(10),20-diene (5c)

Following the procedure outlined for the synthesis of compound (5a), the Grignard reagent prepared from 4-bromo-methoxybenzene was reacted with compound (4) and CuCl in THF to give after workup the required product (5c)

$^1$H NMR (δ, 300 MHz) 0.51 (s, 3H), 1.0-2.9 (m, 21H), 3.78 (s, 3H), 3.60-4.05 (m, 6H), 4.18 (d, J=7.5 Hz, 1H), 4.33 (s, 1H), 6.7-6.9 (m, 3H), 7.08 (d, J=8.5 Hz, 2H).

EXAMPLE 8

21,21-difluoro-11β-(4'-methoxyphenyl)-17,23-epoxy-19,24-dinor-17α-chola-4,9,20-triene (1c)

Following the procedure outlined for the synthesis of compound (1a), the Grignard adduct (5c) was hydrolyzed in 50% sulfuric acid to give after workup the required product (1c).

$^1$H NMR (δ, 300 MHz) 0.57 (s, 3H), 1.2-2.9 (m, 19H), 3.78 (s, 3H), 3.79-4.00 (m, 2H), 4.29 (d, J=6.9 Hz, 1H), 5.75 (s, 1H), 6.81 (d, J=8.8 Hz, 2H), 7.05 (d, J=8.4 Hz, 2H). $^{13}$C NMR (75 MHz) 14.5, 23.6, 25.9, 27.5, 28.4, 31.1, 32.7, 36.9, 39.0, 39.9, 40.8, 48.4 (t, J=2 Hz), 49.9 (d, J=4 Hz), 55.3, 59.5, 65.4, 93.8 (t, J=3.9 Hz), 94.8 (dd, J=17, 19.7 Hz), 114.0, 123.1, 127.9, 129.4, 136.5, 145.8, 151.0 (t, J=281 Hz), 156.5, 157.7, 199.5.

EXAMPLE 9

3,3-Ethlenedioxy-21,21-difluoro-5α-hydroxy-11β-(4'-isopropenylphenyl)-17,23-epoxy-19,24-dinor-17α-chola-9(10),20-diene (5d)

Following the procedure outlined for the synthesis of compound (a), the Grignard reagent prepared from 4-bromomethoxybenzene was reacted with compound (4) and CuCl in THF to give after workup the required product (5d).

$^1$H NMR (δ, 300 MHz) 0.52 (s, 3H), 1.0-3.0 (m, 21H), 2.14 (s, 3H), 3.6-4.0 (m, 6H), 4.23 (d, J=7.1 Hz, 1H), 4.34 (s, 1H), 5.04 (d, J=1.2 Hz, 1H), 5.38 (s, 1H), 7.14 (d, J=8.3 Hz, 2H), 7.36 (d, J=8.3 Hz, 2H).

EXAMPLE 10

21,21-difluoro-11β-(4'-isopropenylphenyl)-17,23-epoxy-19,24-dinor-17α-chola-4,9,20-triene (1d)

Following the procedure outlined for the synthesis of compound (1a), the Grignard adduct (5d) was hydrolyzed in 50% sulfuric acid to give after workup the required product (1d).

$^1$H NMR (δ, 300 MHz) 0.58 (s, 3H), 1.0-2.9 (m, 19H), 2.14 (s, 3H), 3.18 (d, J=30 Hz, 1H), 3.7-4.0 (m, 3H), 4.33 (d, J=7.0 Hz, 1H), 5.06 (d, J=1.3 Hz, 1H), 5.37 (s, 1H), 5.77 (s, 1H), 7.11 (d, J=8.4 Hz, 2H), 7.39 (d, J=8.3 Hz, 2H).

EXAMPLE 11

3,3-Ethylenedioxy-21,21-difluoro-5α-hydroxy-11β-(4'-bromophenyl)-17,23-epoxy-19,24-dinor-17α-chola-9(10),20-diene (5e)

Following the procedure outlined for the synthesis of compound (5a), the Grignard reagent prepared from 1,4-dibromobenzene was reacted with compound (4) and CuCl in THF to give after workup the required product (5e).

$^1$H NMR (δ, 300 MHz).50 (s, 3H), 1.0-2.9 (m, 21H), 3.7-4.0 (m, 7H), 4.17 (d, J=7 Hz, 1H), 4.33 (s, 1H), 7.06 (d, J=8.3 Hz, 2H), 7.36 (d, J=8.5 Hz, 2H).

EXAMPLE 12

21,21-difluoro-11β-4'-bromophenyl)-17,23-epoxy-19,24-dinor-17α-chola-4,9,20-triene (10

Following the procedure outlined for the synthesis of compound (1a), the Grignard adduct (5e) was hydrolyzed in 50% sulfuric acid to give after workup the required product (1g).

$^1$H NMR (δ, 300 MHz) 0.55 (s, 3H), 1.0-2.9 (m, 19H), 3.7-4.0 (m, 3H), 4.27 (d, J=7.1 Hz, 1H), 5.77 (s, 1H), 7.03 (d, J=8.1 Hz, 2H), 7.39 (d, J=8.5 Hz, 2H). $^{13}$C NMR (75 MHz) 14.7, 23.6, 25.9, 27.5, 28.4, 29.2, 31.0, 32.8 (d, J=3 Hz), 36.8, 39.0, 40.2, 40.8, 48.4, 49.72, 49.77, 53.5, 65.4, 93.7 (t, J=4 Hz), 94.73 (dd, J=17, 20 Hz), 119.7, 123.4, 128.8, 129.9, 131.8, 143.8, 144.6, 151.0 (t, J=281 Hz), 156.2, 199.2.

EXAMPLE 13

21,21-difluoro-11β-[4'-(3'-pyridyl)phenyl]-17,23-epoxy-19,24-dinor-17α-chola-4,9,20-triene (1e)

100 mg (0.2 mmol) of (1g), 3-pyridinylboronic acid (60 mg, 0.5 mmol), potassium carbonate (40 mg, 0.3 mmol), bis(triphenylphosphine)palladium(II) chloride (7 mg, 0.01 mmol) and triphenylarsine (7 mg, 0.02 mmol) were dissolved in a mixture of dioxane (5 mL) and water (1 mL) under a nitrogen atmosphere. The reaction mixture was stirred for 3 h at 100 C and then cooled to room temperature. Water (15 mL) was added and the mixture was extracted twice with EtOAc (3×10 mL). The combined organic layers were washed with brine, dried (MgSO$_4$) and evaporated to dryness. Purification by column chromatography using 50% ethyl acetate in hexane afforded 75 mg (75%) of the required product (1e).

$^1$H NMR (δ, 300 MHz) 0.58 (s, 3H), 1.2-2.9 (m, 19H), 3.7-4.0 (m, 2H), 4.39 (d, J=7.1 Hz, 1H), 5.77 (s, 1H), 7.1-7.4 (m, 3H), 7.50 (d, J=8.3 Hz, 2H), 7.8-7.9 (m, 1H), 8.5-8.6 (m, 1H), 8.82 (d, J=1.7 Hz, 1H). $^{13}$C NMR (75 MHz) 14.6, 23.6, 24.7, 25.9, 27.5, 28.4, 31.1, 32.7 (d, J=2.7 Hz), 36.7, 36.8, 39.0, 40.4, 40.7, 48.4 (t, J=1.9 Hz), 49.7, 49.8, 65.3, 93.7 (t, J=3.9 Hz), 94.7 (dd, J=17, 20 Hz), 123.3, 123.6, 127.3, 127.8, 129.7, 134.2, 135.3, 136.1, 144.8, 145.0, 148.1, 148.3, 150.9 (t, J=282 Hz), 156.3, 199.3.

EXAMPLE 14

21,21-difluoro-11β-[4'-(3'-furanyl)phenyl]-17,23-epoxy-19,24-dinor-17α-chola-4,9,20-triene (1f)

Following the procedure outlined for the synthesis of compound (1e), (1e), 3-furanylboronic acid, potassium carbonate, bis(triphenylphosphine)palladium(II) chloride and triphenylarsine were reacted in a mixture of dioxane and water to give, after purification, the required product (1f).

$^1$H NMR (δ, 300 MHz) 0.58 (s, 3H), 1.1-2.9 (m, 19H), 3.6-4.0 (m, 2H), 4.34 (d, J=7.1 Hz, 1H), 5.77 (s, 1H), 6.67 (t, J=0.9 Hz, 1H), 7.15 (d, J=8.2 Hz, 2H), 7.40 (d, J=8.2 Hz, 2H), 7.45 (t, J=1.7 Hz, 1H), 7.70 (s, 1H). $^{13}$C NMR (75 MHz) 14.6, 23.6, 25.8, 27.5, 28.3, 31.0, 32.7 (d, J=2.6 Hz), 36.8, 39.0, 40.4, 40.7, 48.4 (t, J=1.9 Hz), 49.7, 49.8, 65.3, 93.7 (t, J=3.9 Hz), 94.7 (dd, J=17, 19.7 Hz), 108.7, 123.1, 126.0, 126.1, 127.4, 129.5, 130.0, 138.4, 143.4, 143.7, 145.3, 150.1 (t, J=281.5 Hz), 156.4, 199.3.

EXAMPLE 15

Nuclear Receptor Profiling

Determination of the agonist/antagonist nature of the test compounds was carried out using Invitrogen's SELECTSCREEN, a cell-based nuclear receptor profiling service which uses GENEBLAZER a beta-lactamase reporter technology. This assay uses a Beta-lactamase cDNA under transcriptional control of an Upstream Activator Sequence (UAS). The UAS is activated by the GAL4 transcription factor DNA binding domain (DBD), which is expressed as a fusion protein with the target receptor ligand binding domain (LBD). Upon ligand binding, the GAL4(DBD)-NR(LDB) binds to the UAS, which controls transcription of Beta-lactamase. Beta-lactamase cleaves a special engineered fluorescent substrate which results in a change in the measured fluorescence wavelength.

The generalized protocol used for the Progesterone Agonist screen is as follows: The progesterone receptor-LBD-UAS-bla HEK 293T cells were thawed and resuspended in Assay Media (DMEM phenol red free, 2% CD-treated FBS, 0.1 nM NEAA, 1 mM Sodium Pyruvate, 100 U/mL/100 μg/mL Pen/Strep) to a concentration of 468,750 cells/mL. 4 μL of a 10× serial dilution of control agonist R5020 (starting concentration, 100 nM) or test compounds are added to appropriate wells of a 384-well TC-Treated assay plate. 32 μL of cell suspension is added to each well. 4 μL of Assay Media is added to all wells to bring the final assay volume to 40 μL. The plate is incubated for 16-24 hours at 37° C./5% CO2 in a humidified incubator. 84 of 1 μM Substrate Loading Solution is added to each well and the plate is incubated for 2 hours at room temperature. The plate is then read on a fluorescence plate reader (Tecan Safire).

The generalized protocol used for the Progesterone Antagonist Screen, activated by control Agonist R5020 is as follows:

The progesterone receptor-LBD-UAS-bla HEK 293T cells are thawed and prepared as described above for the Agonist screen. 4 μL of a 10× serial dilution of control antagonist RU-486 (starting concentration, 100 nM) or test compounds are added to appropriate wells of a TC-Treated assay plate. 32 μL of cell suspension is added to the wells which is then pre-incubated at 37 C/5% $CO_2$ in a humidified incubator with test compounds and control antagonist titration for 30 minutes. 4 μL of a 10× control agonist (see above) at the predetermined EC80 concentration is added to wells containing the control antagonist or test compounds. The plate is incubated for 16-24 hours at 37 C/5% $CO_2$ in a humidified incubator. 8 μl of 1 μM Substrate Loading Solution is added to each well and the plate is incubated for 2 hours at room temperature. The plate is then read on a fluorescence plate reader (Tecan Safire).

The generalized protocol for the Glucocorticoid Antagonist Screen activated by control Agonist Dexamethasone was carried out as described for the Progesterone Antagonist Screen with the exception that glucocorticoid receptor-LBD-UAS-bla HEK 293T cells were used. The control antagonist used for the glucocorticoid assay was also RU-486.

The results of these tests for the indicated test compounds are shown in Table I

TABLE I

| | Receptor Activity | | |
| | Progesterone | | Glucocorticoid Antagonist |
| Compound | Agonist Activation $IC_{50}$ nM | Antagonist Inhibition $IC_{50}$ nM | Inhibition $IC_{50}$ nM |
|---|---|---|---|
| RU-486 | >10 | 0.664 | 0.583 |
| ZK 230211 | >10 | 0.798 | >10 |
| 1a | >10 | 0.265 | >10 |
| 1b | ND | 0.178 | ND |
| 1c | ND | 0.344 | ND |
| 1d | ND | 0.413 | ND |
| 1e | ND | 0.280 | ND |
| 1f | ND | 0.864 | ND |

ND = not determined

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound of formula (II):

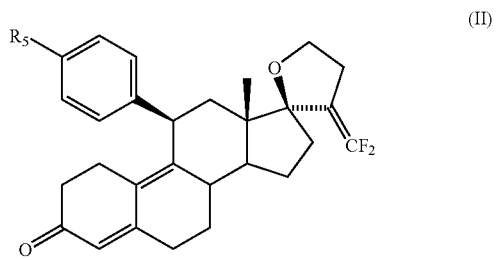

(II)

where $R^5$ is -3-furanyl.

2. A pharmaceutical composition comprising one or more pharmacologically inert carriers and a compound of formula (II):

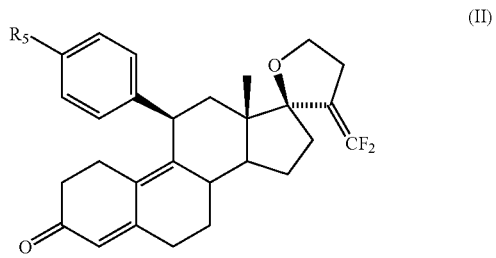

(II)

where $R^5$ is -3-furanyl or -3-pyridyl.

* * * * *